(12) United States Patent
Pulido et al.

(10) Patent No.: US 7,273,445 B2
(45) Date of Patent: Sep. 25, 2007

(54) INTRAOCULAR BRACHYTHERAPY DEVICE AND METHOD

(75) Inventors: Jose Pulido, Brookfield, WI (US); Russell J. Hamilton, Tucson, AZ (US); Gregory L. Walker, Whitestown, IN (US)

(73) Assignee: Board of Trustees of the University of Illinois, Urbana, IL (US)

( * ) Notice: Subject to any disclaimer, the term of this patent is extended or adjusted under 35 U.S.C. 154(b) by 293 days.

(21) Appl. No.: 10/836,140

(22) Filed: Apr. 30, 2004

(65) Prior Publication Data

US 2005/0027156 A1 Feb. 3, 2005

Related U.S. Application Data

(60) Provisional application No. 60/467,085, filed on Apr. 30, 2003.

(51) Int. Cl.
*A61N 5/00* (2006.01)

(52) U.S. Cl. .......................................................... 600/3

(58) Field of Classification Search ................ 600/1–8; 128/897–898
See application file for complete search history.

(56) References Cited

U.S. PATENT DOCUMENTS

| | | | |
|---|---|---|---|
| 5,295,945 A | 3/1994 | Miller | |
| 5,302,168 A | 4/1994 | Hess | |
| 5,498,227 A | 3/1996 | Mawad | |
| 5,540,659 A | 7/1996 | Teirstein | |
| 5,637,073 A | 6/1997 | Freire | |
| 5,643,171 A | 7/1997 | Bradshaw et al. | |
| 5,683,345 A | 11/1997 | Waksman et al. | |
| 5,863,284 A | 1/1999 | Klein | |
| 6,030,333 A | 2/2000 | Sioshansi et al. | |
| 6,050,930 A | 4/2000 | Teirstein | |
| 6,059,713 A | 5/2000 | Urick et al. | |
| 6,099,454 A | 8/2000 | Hastings et al. | |

(Continued)

OTHER PUBLICATIONS

Skolnick, A., Radiation Thereapy for "Wet" Type Macular Degeneration Shows Promise in Early Trials, Mar. 5, 1997, pp. 698-700, vol. 277(9).

(Continued)

*Primary Examiner*—John P. Lacyk
(74) *Attorney, Agent, or Firm*—Husch & Eppenberger LLC; Robert C. Haldiman (57) ABSTRACT

An ocular brachytherapy device, generally comprising a catheter and wire, impregnated with radioactive material, are provided. The wire is formed having a desired treatment shape and size such that it can be placed near an area requiring treatment and effectuate treatment while not affecting adjacent areas. For ease in placement near such areas the wire is preferably formed using materials having properties that permit formation into a desired shape while allowing the wire to be straightened for retraction into the catheter, the shape returning upon removal from the catheter. The wire is preferably impregnated with radioactive material. When the catheter is placed near the area of treatment and the wire is pushed out of the catheter, the wire retakes the desired form and provides a therapeutic radioactive treatment to the area. Preferably, the radioactive material is placed on one edge of the wire, such that the radiation can be directed to the affected area, and non-affected areas can be shielded from radiation.

26 Claims, 5 Drawing Sheets

U.S. PATENT DOCUMENTS

| | | |
|---|---|---|
| 6,110,097 A | 8/2000 | Hastings et al. |
| 6,117,065 A | 9/2000 | Hastings et al. |
| 6,162,428 A | 12/2000 | Snable |
| 6,163,947 A | 12/2000 | Coniglione |
| 6,183,410 B1 | 2/2001 | Jacobsen et al. |
| 6,213,976 B1 | 4/2001 | Trerotola |
| 6,234,951 B1 | 5/2001 | Hastings |
| 6,248,057 B1 | 6/2001 | Mavity et al. |
| 6,264,596 B1 | 7/2001 | Weadock |
| 6,293,899 B1 | 9/2001 | Sioshansi et al. |
| 6,296,831 B1 | 10/2001 | Weller et al. |
| 6,419,621 B1 | 7/2002 | Sioshansi et al. |
| 6,436,026 B1 | 8/2002 | Sioshansi et al. |
| 6,443,881 B1 | 9/2002 | Finger |
| 6,471,630 B1 | 10/2002 | Sioshansi et al. |
| 6,482,142 B1 | 11/2002 | Winkler et al. |
| 6,514,193 B2 | 2/2003 | Kaplan |
| 6,589,502 B1 | 7/2003 | Coniglione et al. |
| 6,699,170 B1 | 3/2004 | Crocker et al. |
| 2001/0024636 A1 | 9/2001 | Weller et al. |
| 2001/0046491 A1 | 11/2001 | Valerie |
| 2002/0131935 A1 | 9/2002 | Fisher et al. |
| 2002/0165218 A1 | 11/2002 | Halbrook et al. |
| 2002/0192280 A1 | 12/2002 | Hunter et al. |
| 2003/0083231 A1 | 5/2003 | Ahlem et al. |
| 2003/0134810 A1 | 7/2003 | Springate et al. |
| 2003/0149327 A1 | 8/2003 | Chin et al. |
| 2003/0157161 A1 | 8/2003 | Hunter et al. |
| 2003/0198798 A1 | 10/2003 | Hehrlein et al. |
| 2003/0208096 A1 | 11/2003 | Tarn et al. |
| 2003/0232013 A1 | 12/2003 | Sieckman et al. |
| 2004/0006305 A1 | 1/2004 | Hebert et al. |
| 2004/0018228 A1 | 1/2004 | Fishell et al. |
| 2004/0138515 A1* | 7/2004 | White et al. .................... 600/3 |
| 2005/0049508 A1* | 3/2005 | Forman et al. ............. 600/476 |

OTHER PUBLICATIONS

Lommatzsch et al., Radiation effects on the optic nerve observed after brachytherapy of choroidal melanimas with $^{106}$Ru/$^{106}$Rh plaques, Springer-Verlag 1994, pp. 232: 482-487.

Finger et al., "Intraocular Radiation Blocking", Investigative Ophthalmology & Visual Science, vol. 32, No. 9, Sep. 1990, pp. 1724-1730.

Schäfer, H. and Vormum, G.: Dosimetry of Ru/Rh-106 ophthalmic applicators. In: *Medical Radiology. Radiotherapy of Intraocular and Orbital Tumors* / ed by Alberti W E and Sagermann R H—Berlin Springer 1993 363-368.

Langmann et al. "Gamma knife radiosurgery for uveal melanomas: an 8-year experience", J. Neurosurg. (Suppl.3)/vol. 93, Dec. 2000, pp. 184-188.

Simonova et al., "Leksell gamma knife treatment of uveal melanoma", J. Neurosurg. (Suppl 5) vol. 97, Dec. 2002, pp. 635-639.

Langmann, et al., "High-compared with low-dose radiosurgery for uveal melanomas", J. Neurosurg (Suppl 5) vol. 97, Dec. 2002, pp. 640-643.

Haas, et al., "Gamma knife treatment of subfoveal, classic neovascularization in age-related macular degeneration: a pilot study", J. Neurosurg (Suppl 3), vol. 93, Dec. 2000, pp. 172-176.

Cohen, "Metastasis-free survival following treatment for uveal melanoma with either stereotactic radiosurgery or enucleation", ACTA Ophthalmol. Scand. 2003, vol. 81, pp. 383-388.

Mueller et al., "Stereotactic Radiosurgery of Large Uveal Melanomas with the Gamma-knife", American Academy of Ophthalmology, vol. 107, No. 7, Jul. 2000, pp. 1381-1388.

* cited by examiner

INTRAOCULAR BRACHYTHERAPY DEVICE AND METHOD

BACKGROUND OF THE INVENTION

The use of radiation to treat retinal and/or choroidal pathology has been investigated. Such radiation therapy, has, however, only been accomplished using either external beam radiation or an external brachytherapy device that is placed on the sclera. One drawback related to these existing therapies is that the retina overlying the choroidal pathology is irradiated as well.

Accordingly, there is a need for an intraocular brachytherapy device and method that reduces the radiation exposure to surrounding tissues. Desirably, such a device permits localized radiation exposure, while shielding surrounding tissues that do not otherwise require exposure. Most desirably, such a device permits placement of the radiation source adjacent the choroidal pathology to cover an area greater than the ingress (e.g., opening or retinotomy) through which the device is passed.

BRIEF SUMMARY OF THE INVENTION

In accordance with the teaching of the present invention, an ocular brachytherapy device, comprising a catheter for delivery of a radioactive treatment proximal to an affected area selected for treatment is provided. An elongated wire having radioactive material thereon is also provided. The wire is formed from a material having a shape memory and is imparted with a desired shape, the wire being re-elongated for insertion into the catheter. In one embodiment, the wire is formed of nickel titanium (NiTi) and is given a watch spring shape, which is uncoiled when reinserted into the catheter.

The wire and catheter are introduced near the affected area and the wire is pushed out from the catheter such that it reforms the desired shape in the vicinity of the area to be treated. In the preferred embodiment, the spring shape of the catheter is reformed upon the wire being pushed from the catheter. In a preferred embodiment of the present invention, a balloon and radio-opaque fluid are used to block the effects of the radioactive material. During treatment, the balloon is inflated with radio opaque fluid such that neighboring tissue is protected during exposure of the area to be treated.

The invention further comprises a method of treating retinal and/or choroidal pathology comprising the steps of providing a catheter for delivery of a radioactive treatment proximal to an affected area selected for treatment and providing an elongated wire having radioactive material thereon, for insertion into the catheter and delivery to the affected area of the eye. The wire is formed from a material having a shape memory and is imparted with a desired shape, the wire being re-elongated for insertion into the catheter. The wire is inserted into the catheter and is subsequently introduced near the affected area. The wire is pushed out from the catheter such that it reforms the desired shape in the vicinity of the area to be treated. The wire is then retained near the affected area for a predetermined period of time to effect treatment. As noted above, in a preferred embodiment blocking means are used to protect neighboring areas from the effects of radiation exposure.

In a preferred embodiment, the wire has a specific width and the radioactive material is placed on one edge of the width. In this manner, the edge with the radioactive material can be placed adjacent the area to be treated keeping areas proximal thereto away from the material by at least the width of the wire. The width of the wire not containing or having been imparted with radioactive material acts to shield adjacent areas from radiation exposure.

The device has beneficial aspects with respect to the treatments noted above as well as with respect to the treatment of age related macular degeneration (AMD). In the treatment of macular degeneration it has been found that treatment, in the manner described herein, that is using treatments such as radiation treatments, can have beneficial effects on visual acuity in patients with AMD. So called Choroidal Neovascularizations (CNV) may be stabilized.

Other beneficial aspects of the present invention will become apparent as the description proceeds.

BRIEF DESCRIPTION OF THE SEVERAL VIEWS OF THE DRAWINGS

The benefits and advantages of the present invention will become more readily apparent to those of ordinary skill in the relevant art after reviewing the following detailed description and accompanying drawings, wherein.

DETAILED DESCRIPTION OF THE INVENTION

While the present invention is susceptible of embodiment in various forms, there is shown in the drawings and will hereinafter be described a presently preferred embodiment with the understanding that the present disclosure is to be considered an exemplification of the invention and is not intended to limit the invention to the specific embodiment illustrated.

An ocular brachytherapy device and method reduces irradiation of the retina by significantly lowering the dose to the retina. Such a device and method permit safer delivery of radiation to the choroid than known irradiation devices and methods. The devices described below and illustrated in the figures and the method disclosed, are used to deliver a dose of radiation, or other treatments, to destroy abnormal tissues, such as the abnormal blood vessels that grow behind the retina in macular degeneration of the eye, and to destroy melanomas, and other tumors, in the eyeball.

Figure 1:
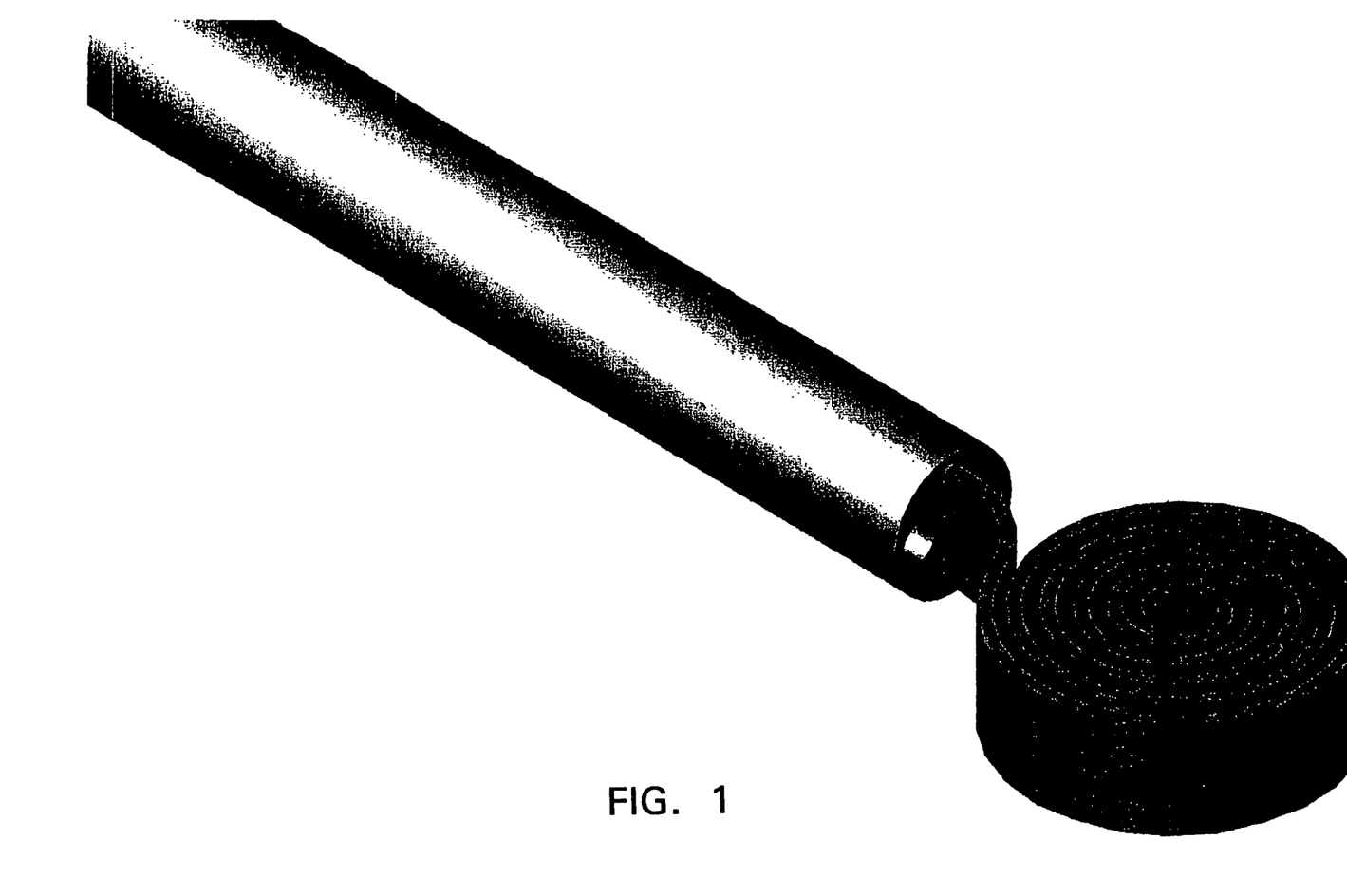
FIG. 1 illustrates one embodiment of an ocular brachytherapy catheter and wire made in accordance with the principles of the present invention.
Figure 2:
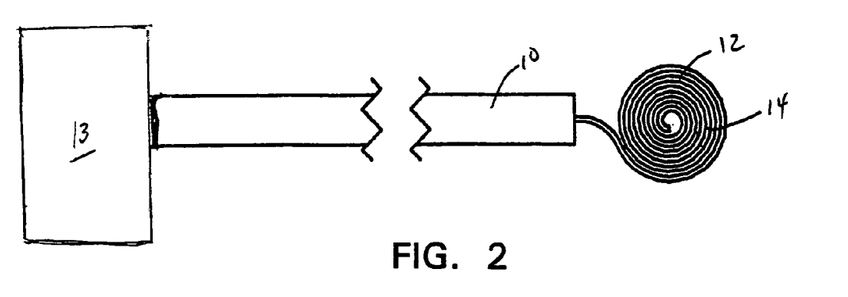
FIG. 2 is a top plan view of the ocular brachytherapy catheter and wire of FIG. 1.

Referring to the figures, FIGS. 1 and 2 show a catheter 10 having a wire 12 therein. The wire 12 is comprised of a material that can take a desirable shape for use in ocular brachytherapy. The shape, while desirable for use in treatment, is unavailing for delivery to the location of the treatment, and is therefore made such that the wire, in which it is formed, can be straightened so that it can be placed within a medical type catheter 10 for delivery to the area of treatment. In a preferred embodiment, the wire is formed in a spiral, or coil spring, shape 14. The coil 14 can be straightened upon being retracted into the catheter, and when pushed out of the catheter retakes the coil spring shape. It is contemplated that the wire, when withdrawn or pulled into the catheter, will be "stored" in a cartridge or cassette 13, illustrated schematically in FIG. 2. In a preferred embodiment the wire is made from an alloy of nickel-titanium (NiTi), however, it will be understood by persons having skill in the art that any metal, or alloy, or other material comprised of desirable properties, including spring steel, shape memory NiTi, super-elastic NiTi, plastics and other metals, can be used to create the wire of the present invention without departing from the novel scope of the present invention.

Figure 3A:
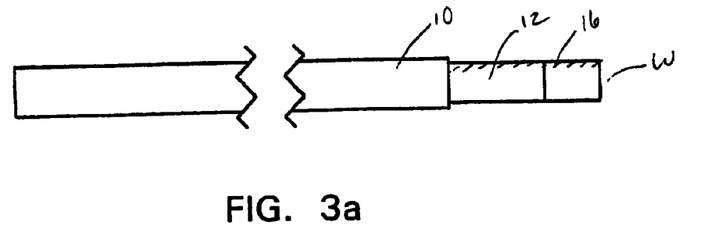
FIG. 3a is a side elevational view of the ocular brachytherapy catheter and wire of FIG. 1.
Figure 8:
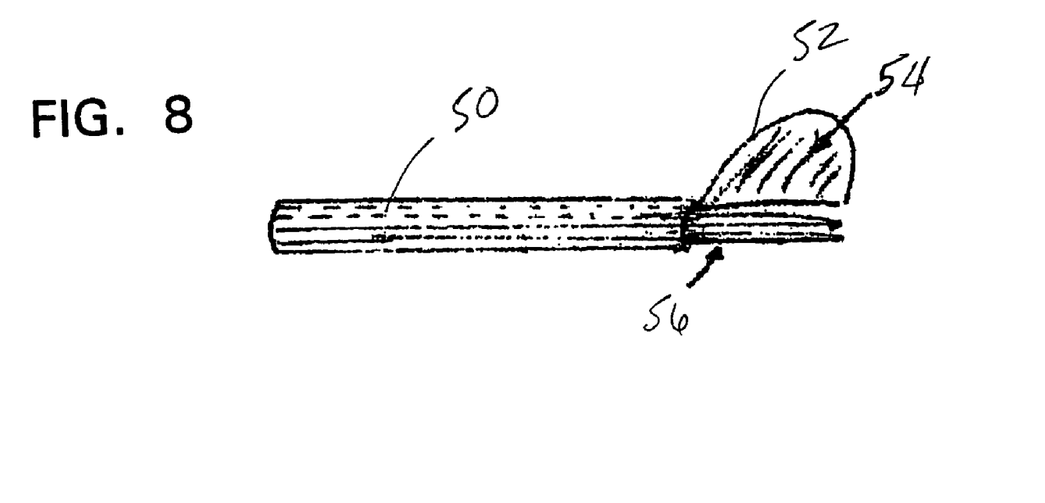
FIG. 8 is a side view of still another embodiment of the brachytherapy catheter.
Figure 9:
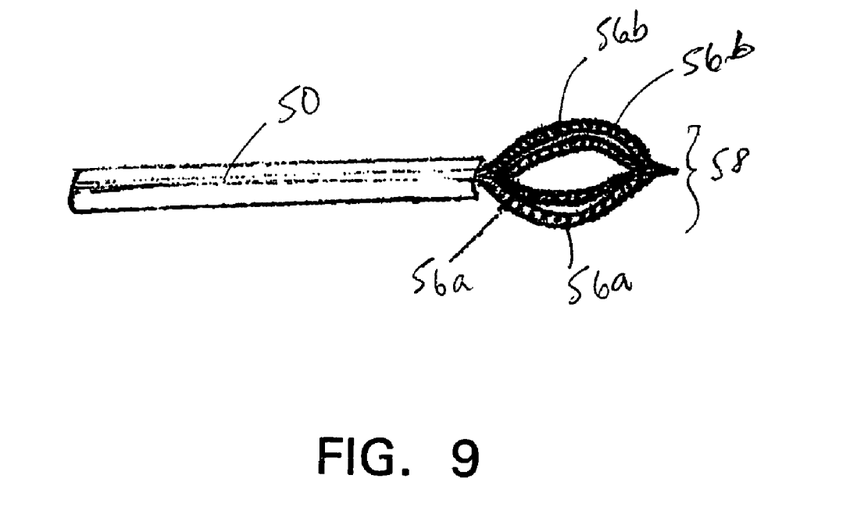
FIG. 9 is a bottom view of the catheter of FIG. 8.

FIG. 3a shows a top view of catheter 10 and wire 12. It can be seen that the wire has a width "W" and that a leading edge 16 of wire 12 is coated, or otherwise treated or overlaid with a radioactive material, as discussed in greater detail below. As will be explained, the leading edge 16 of wire 12 will be placed in proximity with the area to be treated and the remaining volume of wire 12 will act to shield neighboring areas from the radioactive material. In a preferred embodiment, radioactive material, such as phosphorus-32 (P-32) is applied to the metal wire, either as a thin coating or as solid pieces attached to the wire. The wire, or wires (as shown in FIGS. 4, 8 and 9) extend from the tip of the catheter.

Figure 3B:
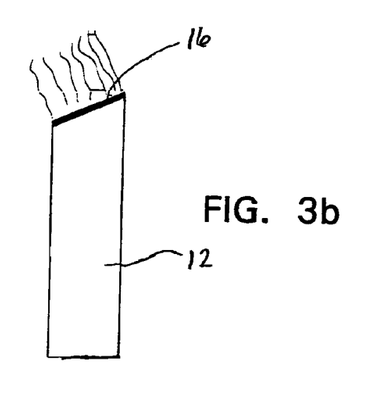
FIG. 3b is a cross-sectional view of one type of wire for use with the catheter of FIG. 1, the wire having a radiation source applied to a beveled edge.
Figure 3C:
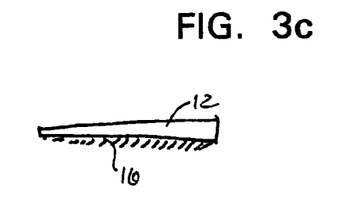
FIG. 3c is a side elevational view of a section of another type of wire for use with the catheter of FIG. 1, the wire having a radiation source applied to an edge.

It will be seen, specifically in FIGS. 3b and 3c, that an edge 16 of wire 12 can be shaped, as desired, to provide a desirable profile as required for the manner of treatment. FIG. 3b shows a cross-section of the wire, or ribbon, which has a beveled edge and radiation applied to the beveled surface along the length of the wire; while FIG. 3c shows a substantially larger, knife edge-type, area for treatment over a greater area. The edge shown in FIG. 3b aids in focusing the radiation imparted thereon inwardly, away from adjacent areas not to be treated, once the wire takes on the coiled form in use. It will be understood by persons having skill in the art that many manners and shapes of leading edges of wires can be utilized to provide a shape consistent with that required or desired for treatment.

It will be understood by persons having skill in the art that a spiral or coil shaped wire segment made with a wire shaped as shown in FIG. 3c may produce a spiral having a somewhat generally hemispherical, or bowl shaped, treatment surface. As a result of this specialized shape, the degree of exposure to radiation can be more carefully controlled, such that areas requiring a smaller dose can be treated by placement of the wire such that the generally lower center of the coil is adjacent such areas. Close, adjacent tissue sections to be treated, requiring a larger dose can then be treated by placement of the outer coil rings, which have a full width of wire and radioactive material closer to the rim of the "bowl". It will be further understood that the wire can be made in any desired shape such that any part of the coil spring has parts that are lower and higher, with respect to the original surface height. In this manner a well mapped area of treatment can be treated effectively by providing desired levels of radiation for accurate exposures based on the height of the wire at a given point. Further, different levels of radiation can be imparted to different sections of the wire to emulate the "bowl" effect, or to enhance the specificity of the treatment further. Exacting treatments of this type, using a coiled, or other shaped wire, having precise mapped sections to match areas of treatment, is contemplated by the device and method of the present invention.

Figure 4:
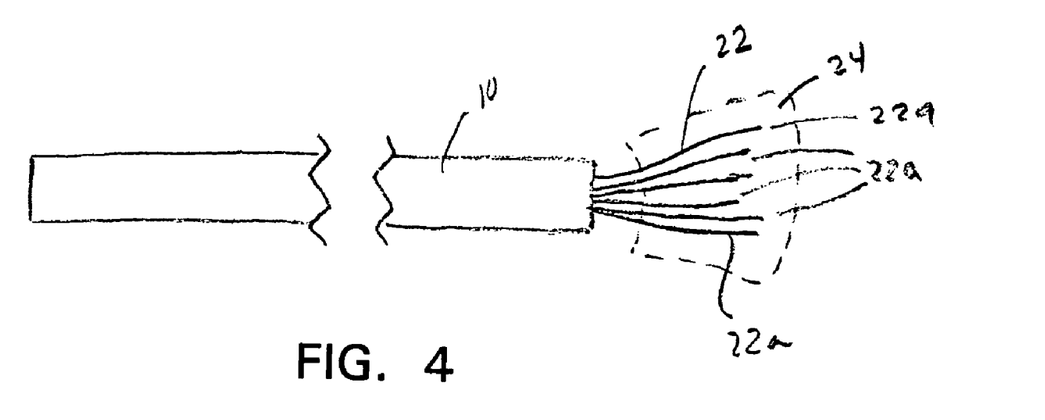
FIG. 4 is another embodiment of an ocular brachytherapy catheter and wire made in accordance with the principles of the present invention.

Referring to FIG. 4, an alternate embodiment of the treatment wire 22 is shown. Wire 22, formed in the shape of a series of tines 22a is shown. An area of radioactive material 24 is expressed as an area surrounded by phantom lines. A catheter 10, similar to that shown in FIGS. 1-3a is shown in association with wire 22. In embodiments, such as the present embodiment, where more than one wire is utilized, the wires can be formed such that when extended from the catheter they can open into a fan shape, a circle, or an desirable shape that will permit the radiation to be more evenly applied to the area of treatment.

A brief discussion of sources and types of radiation and the studies made to determine efficacy of such treatment is helpful to the understanding of the method of using the device of the present invention. The method of using the device of the present invention follows thereafter.

P-32 and Sr-90 were identified as useful sources because they are pure beta emitters that have limited penetration and are easily shielded. The move from considering this device for treating uveal melanomas in addition to macular degeneration was proposed. Since radiation has already been used to treat uveal melanomas, both with external beam radiation and brachytherapy, we could use the results of previous experience to apply the device to these tumors.

First calculating the dose distributions arising from these sources was necessary. Dose calculations were performed for disks of these sources of various diameters (3, 5, 10, and 20 mm) to examine the effective penetration and their possible utility. The results are summarized below for each isotope.

Next, a determination of the dose levels that are needed to treat macular degeneration (blood vessels) and tumors was made. The doses used for eye plaque therapy that has been used successfully for years on uveal melanomas is not relevant for a single fraction application. This is because the eye plaques deliver the dose slowly over a number of days and not at a high rate in one session as we are proposing to do. It is well-known for other tumors that the doses are not the same when the duration and dose rate are changed. Instead, knowledge of the tumor response to radiation applied in a single fraction treatment was needed. A procedure called stereotactic radiosurgery is the application of radiation to treat diseases with a single high dose of external beam radiation. An Austrian group has published a paper on their 8 year history of treating uveal melanomas with this procedure. The effect of this radiation is identical to the effect that the radiation from our device will have, so that comparisons of the dose values can be made directly. The results of this analysis are described below. These same authors reported on their complication rates. This information is important because if doses were to be applied to the same regions, similar complications at the dose levels that they describe would be induced.

There are a few other groups who have also reported on treatment of uveal melanomas with radiosurgery. Based on these papers, there is a slight indication that a dose of 50 Gy to the periphery is appropriate. For this delivery method, the dose in the center is approximately twice this value. The complications in these studies are cataracts and retinopathy, thought to be minor problems, serious complications were neovascular glaucoma, affecting 35% of the patients, and optic neuropathy affecting 20%. These conditions are associated with treating tumors near the ciliary body and juxtapapillary, respectively. There is no certainty of an ability to treat uveal melanomas in either of these regions with the device of the present invention. Since the device applies the dose subretinally, the risk of retinopathy is expected to be much lower. Neuropathy may be avoided since dose is applied on the tumor and does not extend a large distance away.

The doses needed for macular degeneration may also be found by examining the stereotactic radiosurgery literature. For this purpose, the relevant condition is artereovenous malformation (or AVM). This benign condition involves pathological vessel formations. Stereotactic radiosurgery is used to deliver radiation to the vessels in order to obliterate them. Radiation is very effective at doing this. There is a huge amount of data on treating these with radiation, which is well known to persons having ordinary skill in the art. The radiation delivered by the device of the present invention is expected to have the same effect on vessels. An issue is whether vessels in the eye would respond the same as vessels in the brain. The dose needed to obliterate the AVM is 20 Gy, yet higher doses around 30 Gy are used on smaller AVM. These are the peripheral doses with the doses in the center often being twice as large. There is a report of using radiosurgery for macular degeneration (Haas et al, J Neurosurgery 93, 172-76, 2000). They used a dose of only 10 Gy and found that is was not effective. They state that they will next try a dose of 15 Gy. In this case their dose is the peripheral dose with the center being about 10% larger. They are severely limited by retinal complications. The device of the present invention is a clear advantage here.

Source Selection

P-32

Half-life 14.29 days

Beta emission: Single mode with maximum energy 1.710 MeV, average energy 0.695 MeV. Maximum range in: air 730 cm, water 0.8 cm, (for other materials approximately equal to 0.8 cm divided by the density in units of g/cc).

The dose calculations show that this source is adequate for tumors that are less than 4 mm in height.

Source fabrication. Technology exists to implant in Nitinol, making many design configurations possible.

Sr-90

Half-life 29.1 years

Beta emission. Two modes (i) maximum energy 0.546 MeV, average energy 0.196 MeV.

(2) maximum energy 2.284 MeV, average energy 0.935 MeV Maximum range in: air 1062 cm, water 1.1 cm, (for other materials approximately equal to 1.1 cm divided by the density in units of g/cc).

The dose calculations show that this source is adequate for tumors that are less than 6 mm in height (possible to extend to 7 mm if the radiation oncologist is willing to push it).

Source fabrication. Sr-90 sources are used in radiation therapy.

Single Fraction Doses

Treating to its maximal depth with either source results in a significant dose gradient, meaning that portions of the tumor (or any other eye structures not behind the shield) near the face of the source disk will receive a substantially higher dose than the most distal portion. A dose sufficient to kill the tumor must be delivered to the distal portion. A literature review was conducted to determine what doses are needed to control the tumors and whether these doses are expected to cause complications. A report by Langmann et al (Graz Austria group), "Gamma knife radiosurgery for uveal melanomas: an 8-year experience, J Neurosurgery, 93, 184-88, 2000" describes the use of external beam radiation. Similar results are expected if the dose levels applied with the device of the present invention are the same. The paper by the UK group (Cohen et al acta opthalmologica Scandivavica, 81, 383-8, 2003 also describes such a procedure. The reported doses are all over the map in the Austrian paper. The abstract says 45-80 Gy. Paragraphs 3 & 4 of the results state 50 Gy, then adjusted up to 70 Gy, then 50 Gy. The UK paper uses either 50 Gy or 70 Gy. It appears that 50 Gy is a successful dose, although the Austrians state that they are now using a lower dose. The complications associated with these treatments should be avoidable with our device because our radiation dose is placed directly on the tumor and because the device is placed subretinally with shielding of the retina. The radiosurgery treatments are from external sources that must traverse all the normal tissue and structures from the patient's body surface to the tumor. Although a minor treatment complication, our device should not produce a dose large enough to produce cataracts.

Conclusions

A dose of 50 Gy is needed to treat uveal melonomas.

A dose of 30 Gy should obliterate the neovascularization in age-related macular degeneration.

A P-32 device is useful for tumor heights less than 4 mm.

A Sr-90 device is useful for tumor heights less than 7 mm.

A device is expected to be able to deliver these doses safely, that is with doses to critical structures that are lower than reported using stereotactic radiosurgery.

The mean and median tumor heights treated in the above studies were approximately 6.5 mm. Therefore, about half of these tumors are treatable with the Sr-90 our proposed device.

Based on stereotactic radiosurgery treatment of AVM, the device of the present invention should be applicable to neovascularization in age-related macular degeneration.

In the use of a preferred embodiment of the catheter it is contemplated that the device would be associated with a handle or hub with either a slide mechanism to extend and subsequently retract the radioactive wire, a dial to roll up the wire or simply a fitting, such as a Toughy-Burst-type fitting, to permit the wire to be pushed in and then pulled out. When the radioactive wire is not in use, it can be retracted into a portion of the shaft or handle of the catheter, or introducer, equipped with a shielding material to absorb or block the radiation.

When the wire is used in association with a balloon, the balloon would be inserted in a collapsed condition and inflated, using radio-opaque fluids, prior to the extension of the wire to the area to be treated. In this embodiment, the balloon is inflated by means well known in the art, such as those used in angioplasty.

It is contemplated that the present catheter can be used for multiple tissues including but not limited to the eye and parts of the eye.

In use as an ocular brachytherapy device, the device can be used for selective radiation of choroidal neovascular membranes. It is contemplated that prior to surgery, the size of the affected area that requires radiation will be determined by, for example, fluorescein angiography and/or indocyanine green angiography. The size of the catheter device is then selected as appropriate for the size of the area to be treated. An appropriate radiation dose is selected allowing the user to determine the necessary length of (exposure) time, i.e., the length of time that the device is positioned adjacent the affected area. The time of exposure is dependent upon the source activity at the time of treatment. The source strength is selected so that the duration (exposure time) is preferably about 30 seconds to about ten minutes.

For example, following a pars plana sclerotomy, and a pars plana vitrectomy, a small incision is placed in the retina (retinotomy) near the choroidal neovascular membrane and a localized neurosensory detachment is made. The catheter (18-25 gauge) is inserted and positioned in the subretinal space. Once in place the radioactive end is extended and expanded to an appropriate size to cover the affected target area. The source is maintained in place for the desired duration.

Following the desired exposure, the wire is retracted, and the catheter is removed. An air-fluid exchange is then performed and laser photocoagulation is placed around the retinotomy site if necessary. The sclerotomy sites can then be closed using sutures.

Other ocular conditions contemplated for treatment using the present catheter include choroidal melanomas, choroidal angiomas, retinal angiomas, other intraocular angiogenic or neoplastic tissues.

It is also contemplated that a similar or larger sized catheter can be used to treat conjunctival neoplastic or angiogenic growths (for instance pterygia) or to prevent growth of scar tissue into filter blebs following glaucoma procedures. For example, for glaucoma operations or for pterygia, the sclera and the rest of the eye would be shielded and the conjunctiva that requires treatment would be irradiated by placing the device in the subconjunctival space such that the radioactive side is towards the conjunctiva and the shielded side towards the sclera.

It is anticipated that the present catheter can be used for similar procedures to treat tissues and areas other than those related to the ocular system. For use in treatment of these systems, it is anticipated that an incision would be made to properly position the device over the affected tissue, or passed through a body lumen, such as the trachea.

Figure 5:
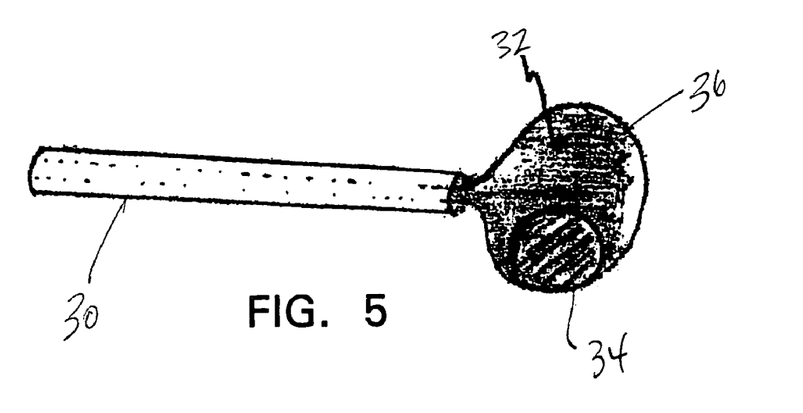
FIG. 5 illustrates another embodiment of an ocular brachytherapy catheter in accordance with the principles of the present invention.

In addition to the device and method previously discussed, and referring to FIG. 5, there is shown another embodiment of the ocular brachytherapy catheter. The brachytherapy catheter includes a catheter 30, and an expandable element, such as a balloon 32. The balloon 32 can include radioactive material on a portion 34 of the balloon surface. The source can be, for example, a phosphorous-32 impregnated region on the balloon surface.

The balloon 32 can be filled with a radio-opaque solution 36 to shield areas other than those in direct exposure to the radiation source on area 34. The solution can be, for example, perfluoroctylbromide, iohexol or perfluoroctane. Other radio-opaque solutions will be recognized by those skilled in the art. Such a radio-opaque solution provides shielding so that only those tissues adjacent the sources are exposed to radiation.

In the use of the present embodiment, the catheter 30 is fed, in a manner known in the art, to near the area to be treated, the balloon 32 is then expanded by filling with the radio-opaque solution. When extended and filled, the balloon 30 can be positioned so that the radio active area 34 can be placed near tissue that requires, or may be helped by, exposure to radiation. The balloon 32 can be expanded so that it is significantly larger than the catheter 30 in which it is that carried. The expanding end of the device, balloon 32, is shielded about its entire surface (by the radio-opaque solution) except for the side to be placed adjacent to the tissue targeted for exposure to the therapeutic radiation. This limits exposure to the surrounding unaffected tissue.

Figure 6:
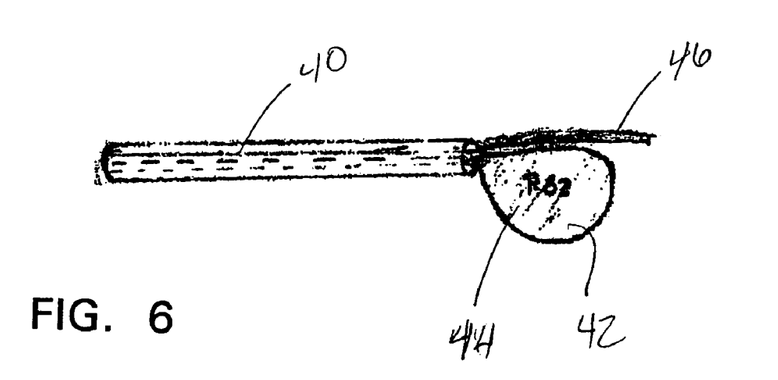
FIG. 6 illustrates a side view of another embodiment of the brachytherapy catheter.
Figure 7:
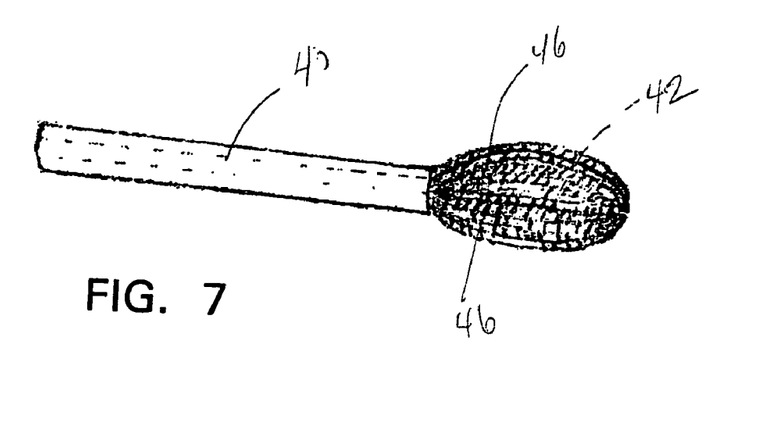
FIG. 7 is a front view of the catheter of FIG. 6.

An alternate embodiment of the brachytherapy catheter is illustrated in FIGS. 6 and 7 which show a side view (FIG. 6) of a device and its top view (FIG. 7). In this embodiment, the balloon 42 is filled with a solution 44 carrying the radiation source (e.g., a solution containing P-32). In this embodiment, the surrounding tissues, of the body being treated, are shielded by tines 46 that extend from the catheter 40. The tines can be configured as a plurality of expanding tines 46 (FIG. 7) that can be extended from and retracted into the catheter 40. The tines 46 can be formed from a metal alloy having a high shape memory and a high atomic number, such as nitinol (Ti—Ni). The tines 46 serve to shield the surrounding tissues from the radiation source when they are fanned out to shield the adjacent areas by covering balloon 42.

Alternately still, the catheter can be configured without the balloon. In such a configuration, the tines can be formed having a coating of a source material (such as P-32) on one side of the tines, thus providing a radiation source from one side of the extended tines, while the other side serves as shielding, again, to prevent exposure to tissues that are not to be subjected to radiation exposure. Thus, the tines themselves provide self-adsorption of radiation. Additional shielding could be provided by incorporating more or extra tines that do not contain P-32 on their surfaces. These layers of tines serve to shield the normal surrounding tissue from the effects of radiation.

Further, in this configuration in which the tines are provided with a coating of the radiation source, additional shielding could be provided by an expanding balloon filled with radio-opaque or radiation-absorbing fluid.

Still another embodiment of the catheter 50 is shown in FIGS. 8-9. This embodiment includes plural sets of tines 56, in which a first set of tines 56a includes a radiation source (again, such as P-32) coated thereon and a second set of tines 56b without the radiation source coating. In this configuration, the second set of tines 56b serves as a shielding layer. Optionally, a balloon 52, containing a radio-opaque solution 54 can be used to provide shielding with or without the second (shielding) layer of tines. As best seen in FIG. 9, the tines can be configured as a mesh 58. It should be noted that in FIG. 9, only two pairs of tines are shown for clarity of illustration, whereas the catheter can include plural sets of tines 56 as needed or desired.

In the present disclosure, the words "a" or "an" are to be taken to include both the singular and the plural. Conversely, any reference to plural items shall, where appropriate, include the singular.

From the foregoing it will be observed that numerous modifications and variations can be effectuated without departing from the true spirit and scope of the novel concepts of the present invention. It is to be understood that no limitation with respect to the specific embodiments illustrated is intended or should be inferred. The disclosure is intended to cover by the appended claims all such modifications as fall within the scope of the claims.

What is claimed:

1. An ocular brachytherapy device, comprising:
   a catheter for deliver of a radioactive treatment proximal to an affected area selected for treatment;
   an elongated wire, having radioactive material on a single edge thereon, the wire being formed from a material having a shape memory and being imparted with a coil spring shape when extended from the catheter, the wire being re-elongated for insertion into the catheter;

the wire and catheter being introduced near the affected area and the wire being pushed out from the catheter such that it reforms the desired shape in the vicinity of the area to be treated;

the wire being placed in the affected area such that the radioactive edge is proximal the area to be treated; and the catheter further comprises a balloon and means to fill the balloon with a radio opaque material so as to provide shielding, against radiation, when the device is used in ocular brachytherapy.

2. An intraocular brachytherapy device, comprising:

a catheter for delivery of a radioactive treatment proximal to an affected area selected for treatment;

an elongated wire having radioactive material thereon, the radioactive material being on a single edge portion of the wire;

the elongated wire being formed from a material having a shape memory and the wire being imparted with a desired shape;

the wire being disposed, at least in part, in the catheter, such that the portion of the wire in the catheter is made generally straight;

the wire and catheter being introduced near the affected area and the wire being pushed out from the catheter such that it reforms the desired shape in the vicinity of the area to be treated.

3. The intraocular brachytherapy device of claim 2 wherein the wire is imparted with a desired shape selected from the group consisting of: a spiral, a coil spring shape, a flat spiral.

4. The intraocular brachytherapy device of claim 2 wherein a second portion of the wire, said second portion not having radioactive material thereon, is disposed to shield the radioactive material.

5. The intraocular brachytherapy device of claim 4 wherein the shielding portion of the wire comprises the edge portion of the wire substantially opposing the single edge portion of the wire having radioactive material thereon.

6. The intraocular brachytherapy device of claim 4 wherein the shielding portion of the wire is comprised of an outer portion of a spiral wire shape.

7. The intraocular brachytherapy device of claim 2 wherein said shape presents a substantially hemispherical face to an area to be treated, at least a portion of said hemispherical face including said single edge portion having radioactive material.

8. The intraocular brachytherapy device of claim 2 wherein said wire has a ribbon shape.

9. The intraocular brachytherapy device of claim 2 wherein said wire is tapered.

10. The intraocular brachytherapy device of claim 2 wherein said wire includes a bevel, said bevel comprising a portion of said single edge portion.

11. The intraocular brachytherapy device of claim 2 wherein said single edge portion has varying amounts of radioactive material applied thereto, said amounts of radioactive material varying along the length of said single edge portion.

12. The intraocular brachytherapy device of claim 2 having a plurality of wires, at least one of said wires having the single edge portion having radioactive material thereon.

13. The intraocular brachytherapy device of claim 2 having at least one wire having the single edge portion with the radioactive material thereon and at least one other wire not having radioactive material thereon, said at least one other wire being disposed to shield the radioactive material.

14. The intraocular brachytherapy device of claim 12 wherein said plurality of wires comprises a mesh.

15. The intraocular brachytherapy device of claim 2 further comprising a balloon.

16. The intraocular brachytherapy device of claim 15 wherein said balloon shields the radioactive material.

17. The intraocular brachytherapy device of claim 16 wherein said balloon shields the radioactive material by means of a radio-opaque filler.

18. The intraocular brachytherapy device of claim 16 wherein said balloon shields the radioactive material by means of a radio-opaque surface portion.

19. The intraocular brachytherapy device of claim 12 further comprising a balloon.

20. The intraocular brachytherapy device of claim 2 wherein said radioactive material is selected from the group consisting of: P-32 and SR-90.

21. The intraocular brachytherapy device of claim 2 wherein said wire is nickel titanium (NiTi).

22. The intraocular brachytherapy device of claim 2 wherein said wire is comprised of nickel titanium (NiTi) and the radioactive material is selected from the group consisting of P-32 and SR-90.

23. The intraocular brachytherapy device of claim 2 wherein the device is constructed with a handle selected from the group consisting of: a slide mechanism, a dial mechanism, a fitting, and a Toughy-Burst type fitting.

24. The intraocular brachytherapy device of claim 17 wherein the balloon is filled with a solution selected from the group consisting of perfluoroctylbromide, ilhexol and perfluoroctane.

25. The intraocular brachytherapy device of claim 2 wherein said device is dimensioned and arranged for intraocular applications.

26. The intraocular brachytherapy device of claim 2 wherein said device is dimensioned and arranged for a subretinal application.

* * * * *